United States Patent [19]
Priddy et al.

[11] Patent Number: 5,554,268
[45] Date of Patent: Sep. 10, 1996

[54] DISPOSABLE SENSOR FOR METAL ANALYSIS

[76] Inventors: Richard V. Priddy, 6507 Darnall Rd., Baltimore, Md. 21204; John C. Schmidt, 2702 Superior Ave., Baltimore, Md. 21234; John E. Studer, Jr., 106 Burnham Rd., Morris, N.J. 07950

[21] Appl. No.: 392,364

[22] Filed: Feb. 22, 1995

[51] Int. Cl.$^6$ .................................................. G01N 27/26
[52] U.S. Cl. ........................ 204/400; 204/409; 204/434; 205/775
[58] Field of Search ................................. 204/153.1, 400, 204/434, 409

[56] References Cited

U.S. PATENT DOCUMENTS

| | | | |
|---|---|---|---|
| 3,055,759 | 9/1962 | Busby et al. | 204/153.1 |
| 3,100,164 | 8/1963 | Solomon et al. | 429/116 |
| 3,170,860 | 2/1965 | Morin | 204/400 |
| 3,211,638 | 10/1965 | Halvorsen | 204/415 |
| 3,904,487 | 9/1975 | Lieberman et al. | 204/434 |
| 4,146,436 | 3/1979 | Kellerman et al. | 204/434 |
| 5,098,545 | 3/1992 | Patko | 204/415 |
| 5,292,423 | 3/1994 | Wang | 204/434 |

FOREIGN PATENT DOCUMENTS

WO9108474  6/1991  United Kingdom .

*Primary Examiner*—T. Tung
*Attorney, Agent, or Firm*—Leonard Bloom

[57] ABSTRACT

A disposable sensor for metal analysis comprises a housing including a first section, a second section, and a flexible intermediate section therebetween. An ampoule containing a reagent is disposed in the intermediate section. A liquid seal is formed between the first and second sections. The intermediate section of the housing of the disposable sensor may be flexed to break the ampoule. When the seal is broken between the first and second sections, and the water sample mixes with the reagent, the mixture flows into the second section containing an electrode assembly. The electrode assembly may be disposed in engagement with the monitoring device to determine the concentration of the at least one metal in the water sample.

22 Claims, 7 Drawing Sheets

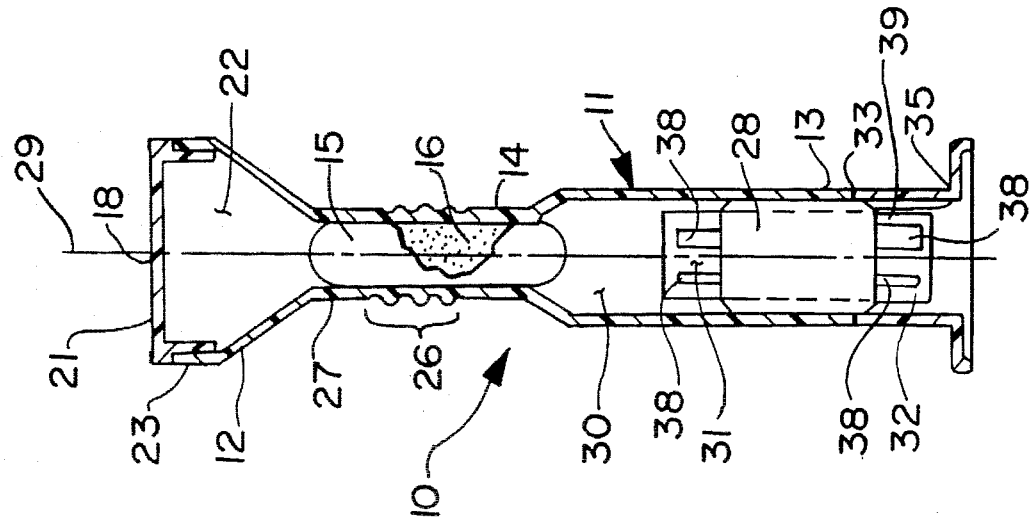
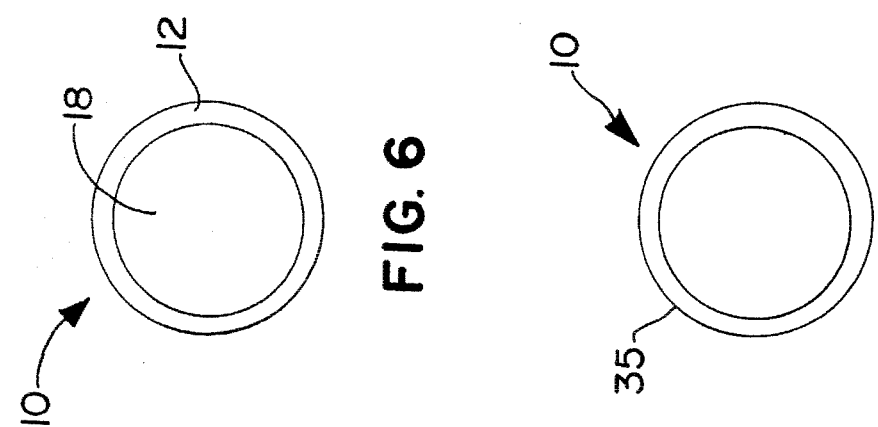
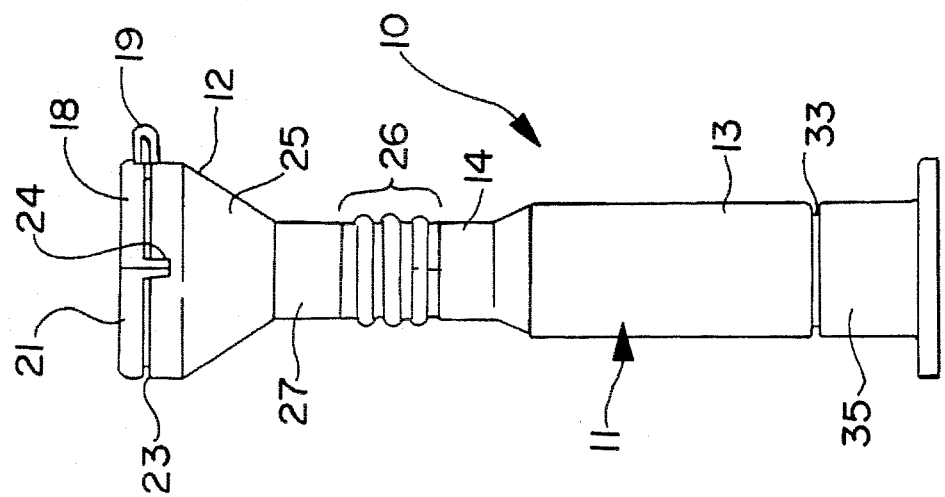

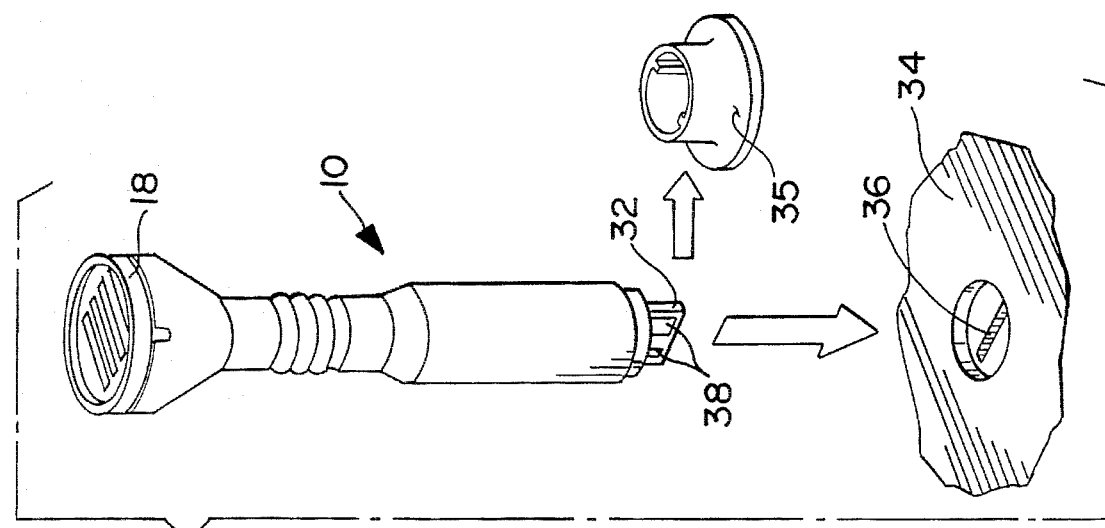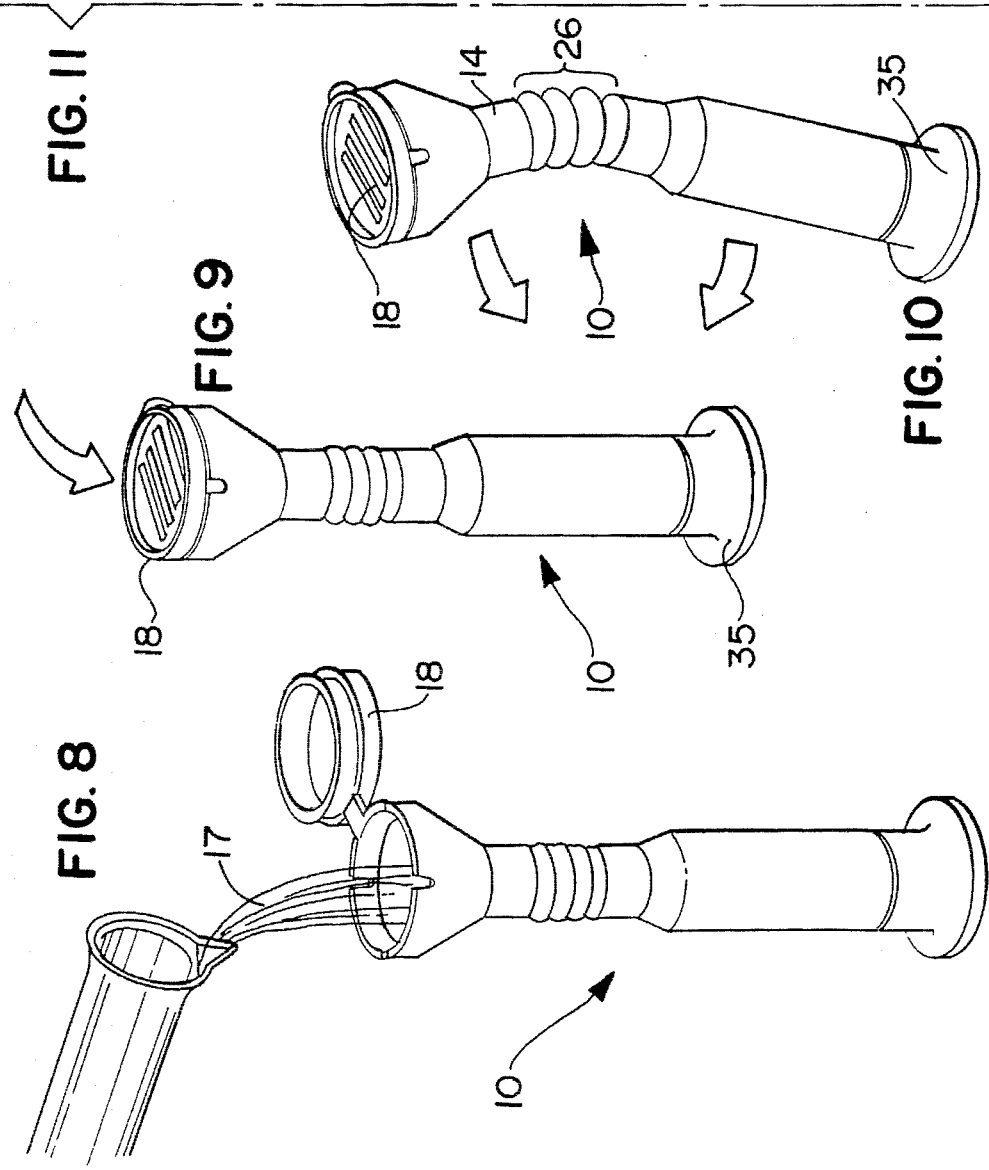

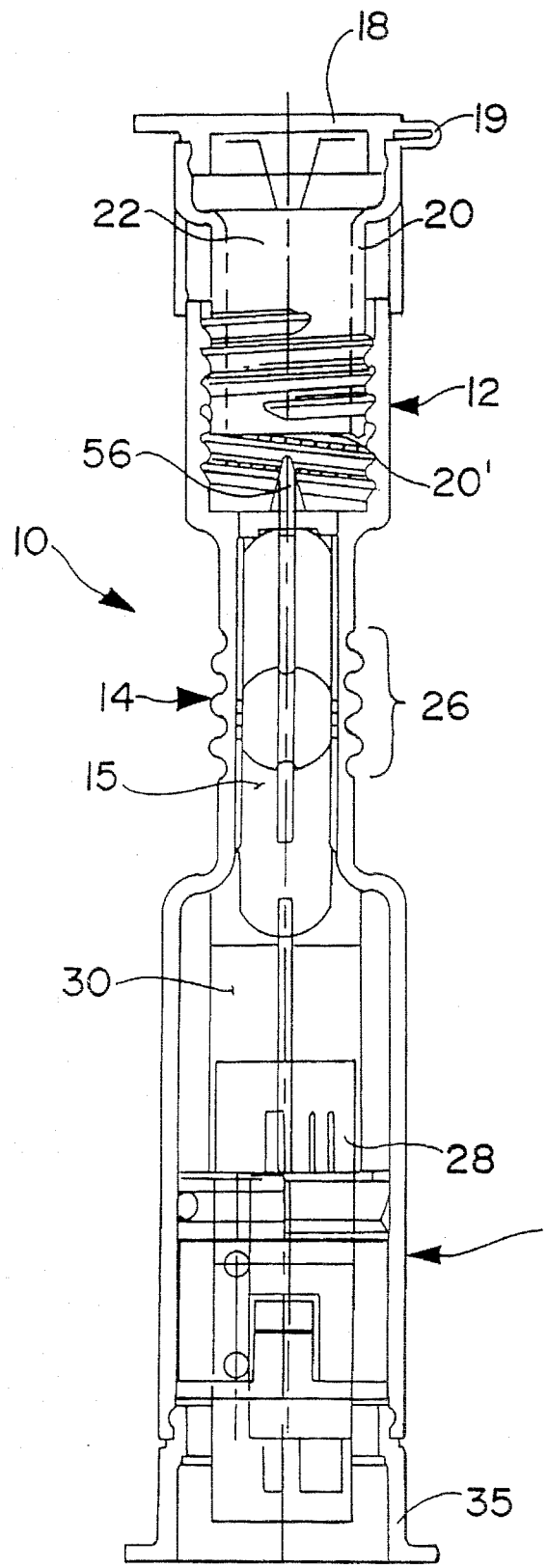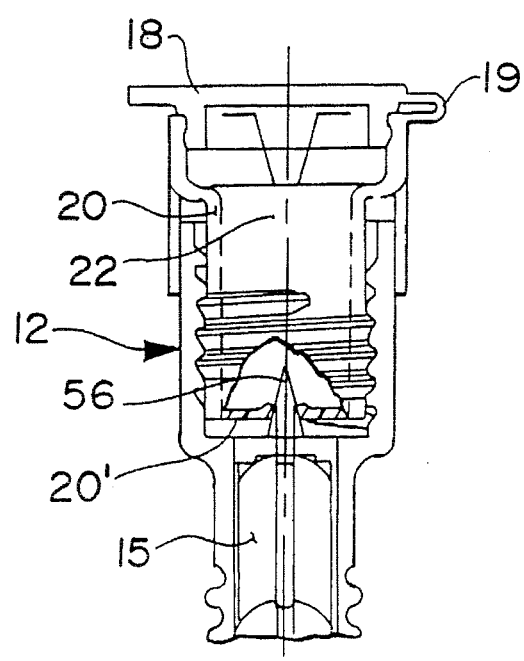
FIG. 12
FIG. 13

1

DISPOSABLE SENSOR FOR METAL ANALYSIS

FIELD OF THE INVENTION

The present invention relates to an apparatus and method for detection of metals in water, and more particularly, to a portable disposable sensor which can be used even by non-technical personnel in the field for accurate measurement of levels of metals in water samples.

BACKGROUND OF THE INVENTION

It is known that the presence of even very low levels of certain metals in water consumed in everyday life of people, in agriculture and for other purposes is a significant factor causing serious health problems throughout the world. The metals may contaminate water as the result of environmental pollution and because of natural reasons.

Metal analysis usually involves a sophisticated and expensive equipment. This equipment is difficult to use in the field, because the instrumentation required is large and delicate, and the analysis requires precise measurement and mixing of numerous types of liquid without contamination.

Usually, water samples are transported from sample locations to a laboratory to be subjected to the analysis. Since a significant amount of time may elapse during the transportation of the water sample to the laboratory, the sample characteristics may change as a result of precipitation, absorption, and/or contamination during this period.

Concerned institutions and individuals are continually looking for economical, accurate and simple-to-use solutions for trace metal analysis in the field. Nevertheless, a small number of colorimetric kits are available which can be used in the field to measure the concentration of a single metal, and no kits are available which allow measurement of several metals simultaneously.

SUMMARY OF THE INVENTION

It is, therefore, an object of the present invention to provide an inexpensive and simple-to-use apparatus and method for accurate and fast metal analysis.

It is another object of the present invention to provide a disposable sensor which can be used even by non-technical personnel for determining the concentration of one or several metals in a water sample directly in the sample location (in the field).

It is still another object of the present invention to provide a disposable sensor which may be disposed in engagement with the monitoring device (reader), and which contains pre-mixed reagent, automatically meters the proper volume of a water sample and automatically mixes the solutions, thereby avoiding any possible foreign contaminations.

The present invention finds its particular utility as a disposable sensor working in combination with a monitoring device for metal analysis.

According to the teachings of the present invention, the disposable sensor comprises a plastic housing including a first section, a second section, and a flexible intermediate section therebetween. An ampoule, containing a reagent, is disposed in the intermediate section, and may form a liquid seal between the first and second sections. Alternatively, the liquid seal may be formed by a thin membrane above the ampoule. It will be understood by those skilled in the art that in lieu of an ampoule a thin bag, pouch, or thin molded section (containing a reagent and which can be ruptured by flexing the disposable sensor) may be used. The water sample is disposed in the first section, and an electrode is disposed in the second section. When the intermediate section of the housing of the disposable sensor is flexed to break the ampoule and the seal is broken between the first and second sections, the water sample mixes with the reagent and flows into the second section containing the electrode. The electrode may be disposed in engagement with the monitoring device to determine the concentration of the metal in the water sample.

The first section of the housing also includes a top cavity for measuring the water sample. Funnel shaped walls surround the top cavity. An upper edge of the funnel shaped walls comprises at least a pair of side notches spaced apart along said upper edge. Once the water sample is poured into the top cavity, a top cap removably secured to the first section, forces excess water out of said notches, such that the top cavity contains the water sample of a predetermined volume.

The intermediate section of the housing includes side walls having a series of annular ribs spaced apart longitudinally. The annular ribs provide additional flexibility to the intermediate section of the housing to facilitate breaking of the frangible ampoule while flexing the housing along its longitudinal axis.

The second section of the housing has a lower chamber for receiving a mixture of the water sample and the reagent. The electrode includes a first portion secured within the lower chamber, and a second portion, such that once the first portion of the electrode is immersed into the mixture of the water sample and the reagent, the electrode emits an electrical signal corresponding to the concentration of the metal in the water sample (once a proper electrical potential is supplied from the monitoring device to the electrode).

The second portion of the electrode protrudes externally from a lower edge of the second section of the housing to engage the monitoring device. A protective cap is removably secured to the lower edge of the second section of the housing, such that when the protective cap is removed, the second portion of the electrode may engage the monitoring device. The monitoring device reads the emitted signal and the concentration of the metal in the water sample determined by the monitoring device is displayed by a display of the monitoring device.

In an alternative embodiment, the housing includes a molded plastic part extending within the housing substantially through the intermediate section and the second section of the housing. A narrow space left between the molded plastic part and a side wall of the housing serves to secure the ampoule in the proper orientation. A slot is formed in the lower end of the molded plastic part such that the electrode is secured within said slot.

Viewed in another aspect, a disposable sensor comprises at least one electrode, a cylindrical housing secured to said at least one electrode by a lower end, and a cap removably secured to a top end of the cylindrical housing. The top end of the cylindrical housing has a plurality of circumferentially-spaced metering holes. The cap has a cylindrical sleeve and a top surface. A plurality of holes are disposed across the top surface of the cap. An ampoule, containing a reagent, is disposed above the top surface of the cap and is secured to the cap by a flexible cover. When water sample is poured in the housing and the cap is secured to the housing, the cylindrical sleeve on the cap seals the metering holes in the housing. The flexible cover may be flexed to break the ampoule, such that the reagent is forced into the housing through said holes in the top surface of the cap, and such that the water sample mixes with the reagent in the housing. The electrode may be disposed in engagement with the monitoring device to determine the concentration of said at least one metal in the water sample.

These and other objects of the present invention will become apparent from a reading of the following specification taken in conjunction with the enclosed drawings.

BRIEF DESCRIPTION OF THE DRAWINGS

FIG. 4 is a side view of the disposable sensor of the present invention.

FIG. 5 is a longitudinal sectional view of the disposable sensor of the present invention.

FIG. 6 is a top view of the disposable sensor of the present invention.

FIG. 7 is a bottom view of the disposable sensor of the present invention.

FIGS. 8–11 show the steps of a metal analysis in sequence.

FIGS. 12 and 13 show another embodiment of the present invention.

DETAILED DESCRIPTION OF THE INVENTION

Figure 1:
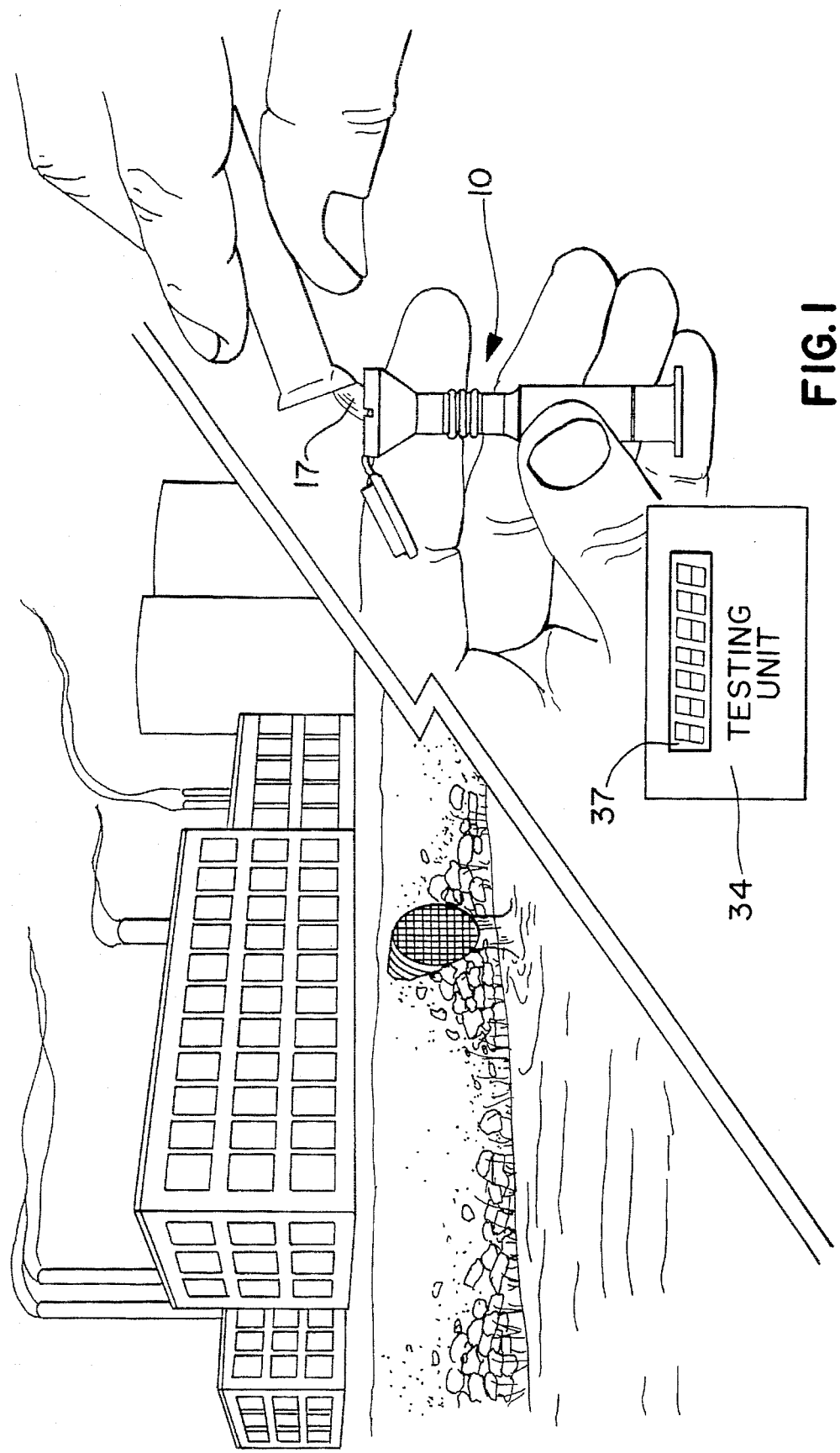
FIG. 1 is a pictorial view showing analysis conducted in the field.
Figures 2, 3:
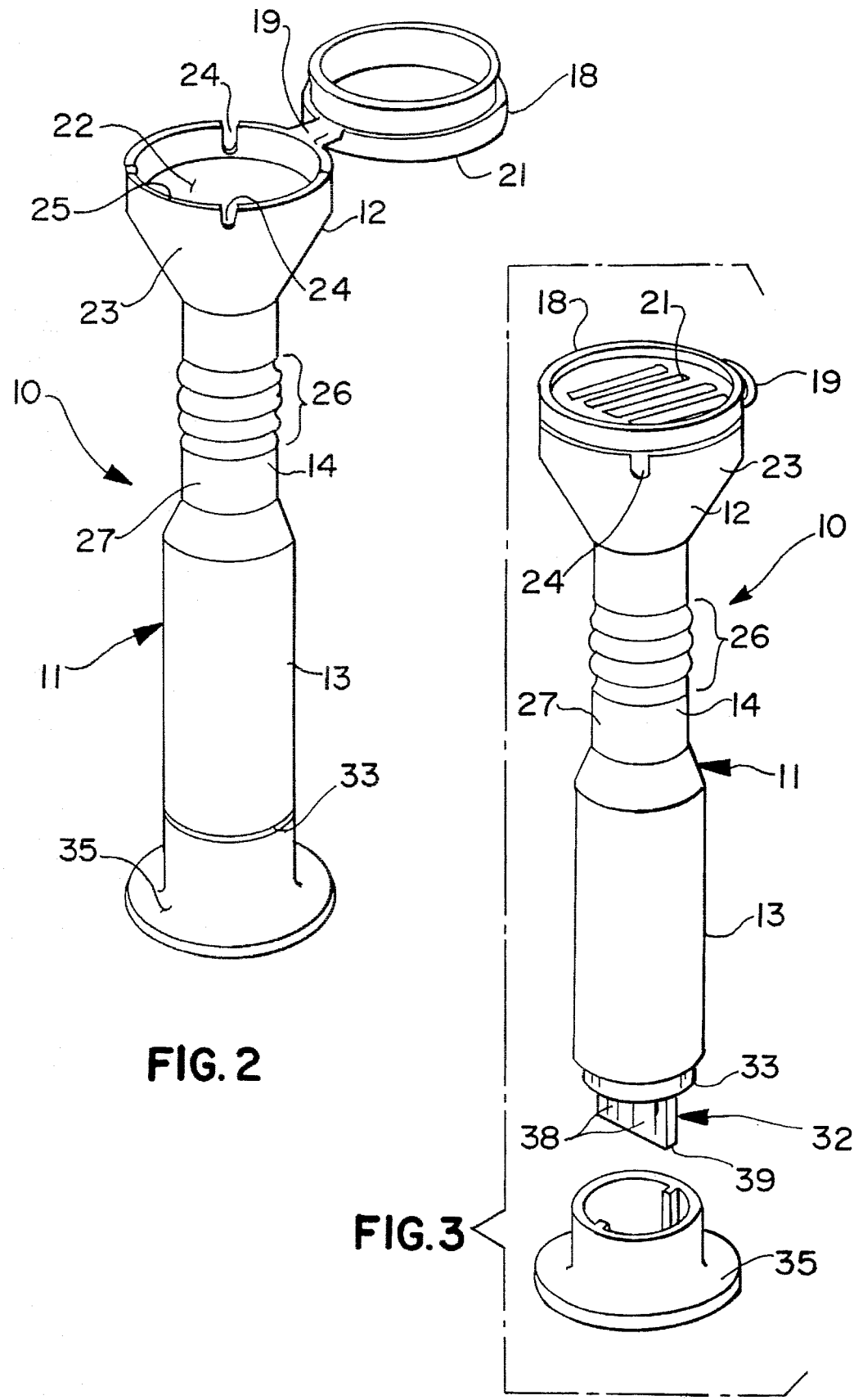
FIG. 2 is a perspective view of a disposable sensor of the present invention.
FIG. 3 is another perspective view of the disposable sensor of the present invention.

Referring to FIGS. 1–11, a disposable sensor 10 comprises a plastic housing 11 which has three sections: a first (or top) section 12, a second (or lower) section 13, and an intermediate section 14 connecting the top section 12 and the lower section 13. An ampoule 15 is held in the intermediate section 14. The ampoule 15 contains a reagent 16 which is pro-mixed to form a solution with a water sample 17 poured into the top section 12 of the housing 11. The ampoule 15 forms a liquid seal between the top section 12 and the lower section 13.

Alternatively, the liquid seal may be formed by a thin membrane above the ampoule which is ruptured as shown in FIG. 13. A typical reagent for the measurement of lead and copper in water includes hydrochloric acid and sodium chloride in water.

A top cap 18 is secured to the top section 12 of the housing 11 by a living hinge 19.

The top section 12 has a top cavity 22 which has a funnel shape for easy pouring of the water sample 17 and is surrounded by funnel shaped walls 23. A pair of side notches 24 is disposed at an upper edge 25 of the funnel shaped walls 23. When the water sample 17 is poured into the top cavity 22 and the top cap is closed, any excess water, being squeezed by the top cap 18, runs out the notches 24. The top cavity 22 is designed and dimensioned in such a manner, that the disposable sensor 10 always containing the proper volume of fluid after it is filled.

In the alternative embodiment, best shown in FIGS. 12 and 13, the first section 12 of the housing 11 includes a separate top portion 20 having a top cavity 22 for receiving and holding the water sample 17. This piece of plastic 20' serves as a bottom of the separate top portion 20 and provides liquid sealing. When the water sample 17 is poured into the top cavity 22 of the separate top portion 20 and the top cap 18 is closed (as shown in FIG. 12), the separate top portion 20 is screwed down, and a piercing point 56 ruptures the plastic 20' (as shown in FIG. 13). Thereby, water flows down, and may be mixed with the reagent. In this embodiment, the fluid seal is provided above the ampoule, and fluid seal around the ampoule is not required.

Means including a molded plastic part is located within the housing to provide a proper orientation for the ampoule.

The intermediate section 14 of the housing 11 has a series of annular ribs 26 spaced apart longitudinally along side walls 27 of the intermediate section 14.

The annular ribs 26 provide additional flexibility to the intermediate section 14 of the housing 11 to facilitate breaking of the ampoule 15 while flexing the housing 11.

Alternatively, the ampoule can be replaced with a thin bag, pouch, or thin molded section, all of which can be ruptured by flexing the disposable sensor.

The lower section 13 of the housing 11 has a lower chamber 30 for receiving the water sample 17 mixed with the reagent 16 when the ampoule 15 is broken. A first portion 31 of the electrode assembly 28 is secured within the lower chamber 30 by means known-by those skilled in the art. A second portion 32 of the electrode assembly 28 protrudes externally from a lower edge 33 of the second section 13 of the housing 11 to engage the monitoring device 34.

A protective cap 35 is removably secured to the lower edge 33. When the disposable sensor 10 engages the monitoring device 34, the protective cap 35 is removed and the second portion 32 of the electrode assembly 28 is inserted into the receiving portion 36 of the monitoring device 34.

The electrode assembly comprises a series of electrodes 38 on a nonconductive substrate 39, as best shown in FIG. 5.

The monitoring device 34 may operate the disposable sensor 10 by any means known to those skilled in the art, such as disclosed in U.S. Pat. No. 5,292,423.

The electrical signal may be emitted during the supplying of the proper electrical potential or after the electrical potential is applied, depending on the type of analysis being conducted.

Referring now to FIGS. 8–11, in order to conduct an analysis of the water sample 17, a technician should perform the following steps:

1. remove the top cap 18 in order to open the top cavity 22 and to pour the water sample 17 into the top cavity 22 (FIG. 8);
2. close the top cap 18, thereby the cover portion 21 of the top cap 18 presses the meniscus on the upper surface of the water sample 17 and squeezes out any excess water through the side notches 24 (FIG. 9);
3. flex the ribbed intermediate section 14 along the axis of the sensor 10 (FIG. 10), thereby breaking the ampoule 15 and breaking the seal between the top section 12 and the lower section 13 of the housing 11. The water sample 17 mixes with the reagent 16 and flows into the second (lower) section 13 containing the electrode 28 to fill the lower chamber 30;

4. remove the protective cap 35 and to dispose the disposable sensor 10 in engagement with the monitoring device 34, such that the second portion 32 of the electrode assembly 28 is inserted into the receiving portion 36 of the monitoring device (FIG. 11);

5. activate the monitoring device, which automatically applies the proper potential to the electrode assembly 28 (the monitoring device reads the emitted signal by the electrode assembly 28 and converts it to a concentration of the metals, which is displayed);

6. read the concentration of the metal shown by the display 37.

Figure 14:
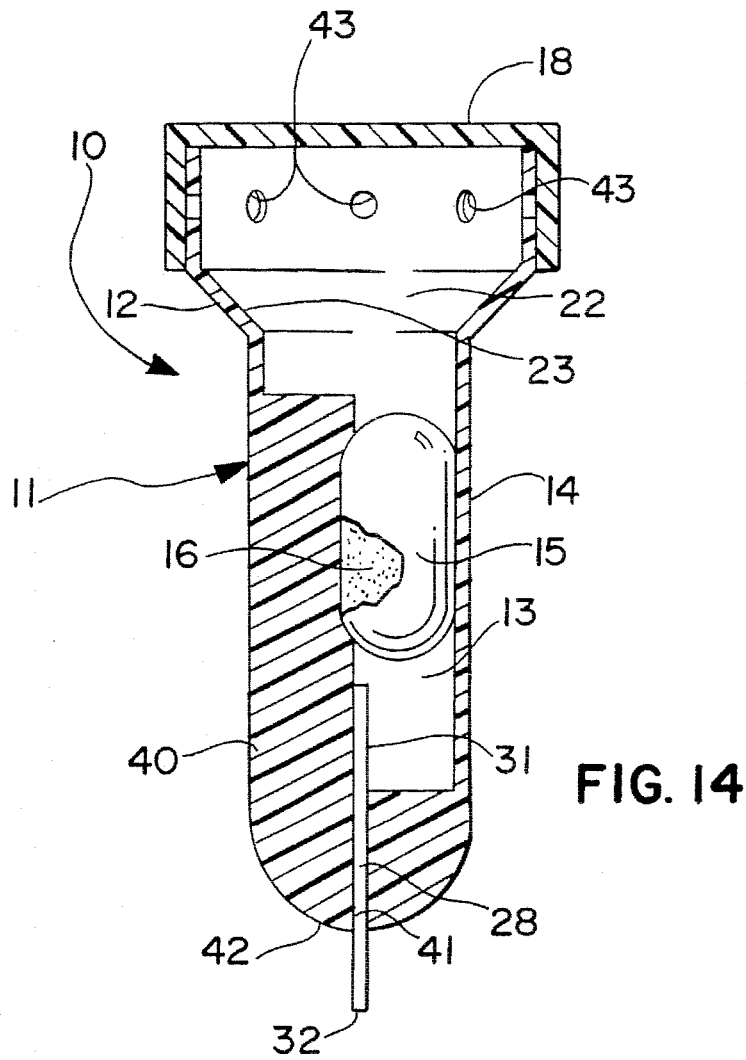
FIG. 14 is another embodiment of disposable sensor of the present invention.
Figure 15:
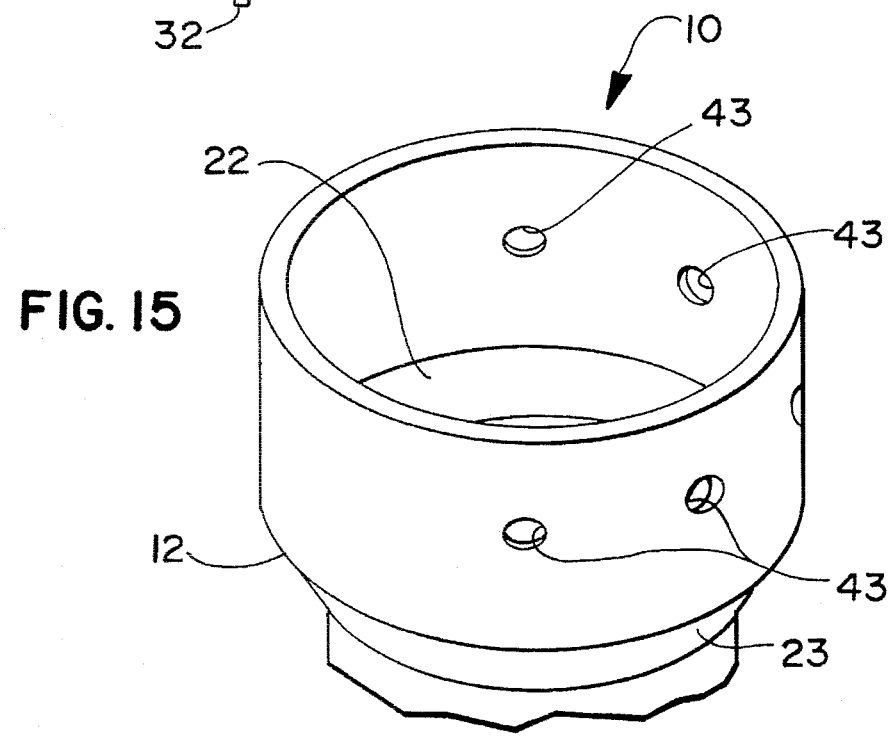
FIG. 15 is an enlarged partial perspective view of a top section of the sensor shown in FIG. 14.

Another embodiment of the present invention is shown in FIGS. 14 and 15. The disposable sensor 10 includes a plastic housing 11 having the first section 12, the second section 13 and the intermediate section 14, wherein the ampoule 15 with the reagent 16 is held. The plastic housing 11 is a self-metering tube (SMT) having a molded plastic part 40, which includes a slot 41 in its lower end 42, such that the electrode assembly 28 can slide through the slot 41. In the first (or upper) section 12 of the housing 11, fluid level holes 43 for excess water to flow out are disposed. In order to conduct the analysis, it is necessary to perform the following steps:

1. remove the top cap 18;
2. pour the water sample into the top of the tube until the water flows out the fluid level holes 43;
3. if the tube does not fill completely due to trapped bubbles, to tap it gently dislodge the bubbles and add additional sample until the water sample flows out the fluid level holes 43;
4. replace the top cap 18;
5. squeeze the tube until the ampoule 15 is broken;
6. shake the tube for 5 seconds to mix the reagent 16 and the water sample 17;
7. insert the electrode assembly's electrical connector (second portion 32) into the receiving portion 36 of the monitoring devices 34, and activate the monitoring device 34.

This embodiment has most of the advantages of the disposable sensor 10 shown in FIGS. 1–11.

Figures 16, 17:
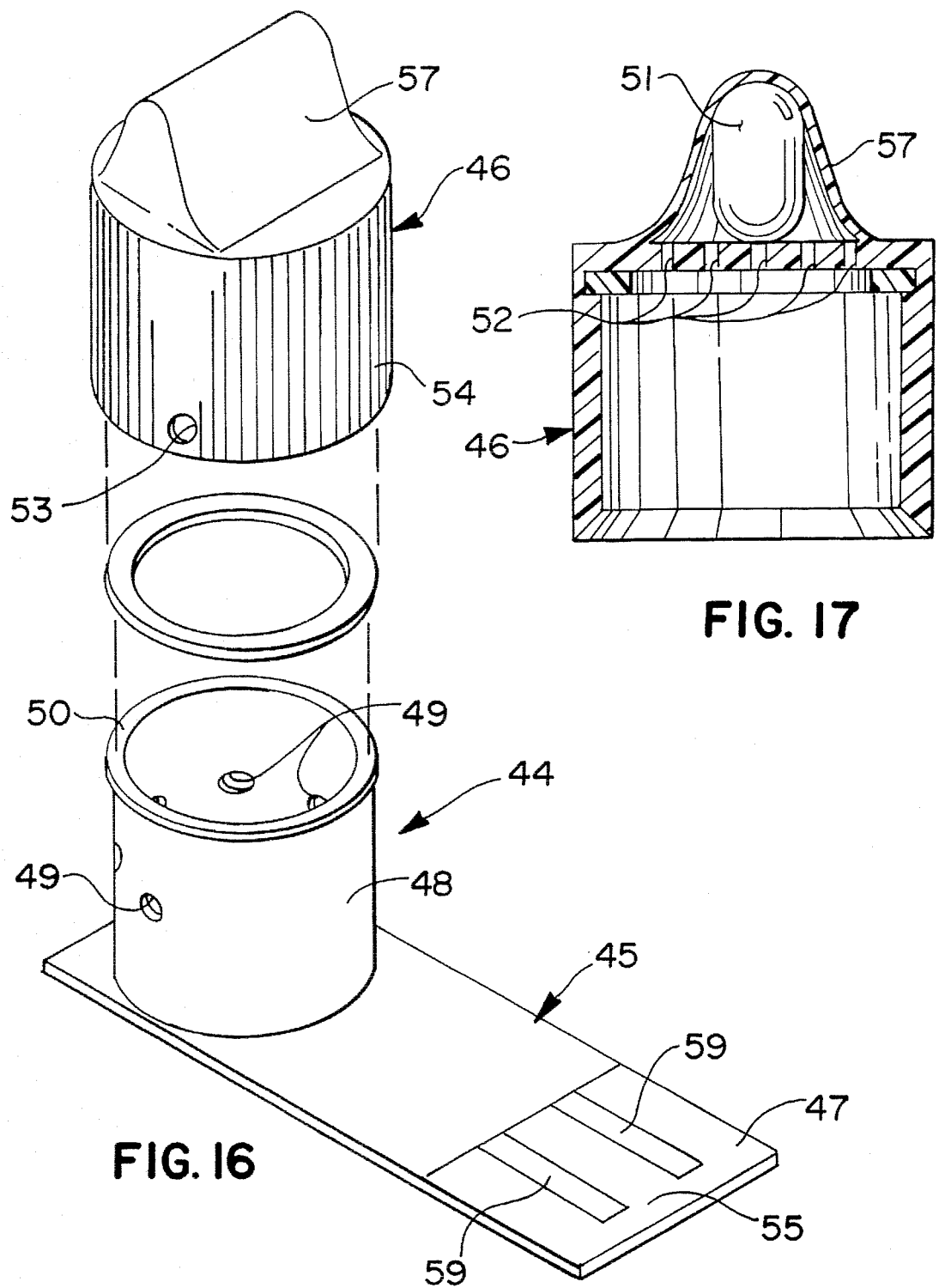
FIG. 16 is an exploded perspective view of yet another embodiment of the present invention.
FIG. 17 is a longitudinal cross-sectional view of the sensor shown in FIG. 16.

Shown in FIGS. 16 and 17, the disposable sensor 44 (or a self-metering vial), consists of two parts: an electrode assembly 45 and a reagent cap 46.

The electrodes assembly 45 consists of a pair of electrodes 59 on a non-conductive substrate 47. A tube 48, containing metering holes 49, is attached over the electrode 45. The water sample is poured into the top 50 of the tube 48. The water fills the tube 48 until it reaches the holes 49 after which any excess water spills out the holes 49.

The reagent cap 46 contains an ampoule 51 filled with the reagent currently used to measure cadmium, lead, and copper. The ampoule is secured to the cap 46 by a cover or "reagent bubble" 57. Four holes 52 in the cap 46 under the ampoule 51 allow the reagent to flow into the vial 44 and mix with the water sample. Another hole 53 near the edge of the cap 46 is covered with Gore-Tex®, and acts as a vent. The height of the cap 46 forms a seal over the vial holes 49, and prevents solution from escaping the vial 44 during mixing of the solution.

The following steps serve as an example of how this disposable sensor might be used:

1. remove the reagent cap 46 from the vial 44;
2. hold the electrode surface parallel to the ground. Pour water into the top 50 of the vial 44 until water flows out of all five holes 49;
3. place the reagent cap 46 on the top 50 of the vial 44;
4. crush the reagent ampoule 51 and press the plastic ampoule cover flat 57, so all of the reagent is forced into the vial 44;
5. shake the electrode-cap assembly for 15 seconds to mix the water sample and the reagent;
6. turn the reader 34 on and wait for the reader 34 to indicate that it is ready. Insert the end 55 of the electrode assembly 45 into the reader, and push and start button on the reader 34;
7. record the results, which will be displayed on the LCD 37 of the reader;
8. remove the electrode-cap assembly from the reader.

The self-metering disposable sensor shown in FIGS. 16, 17 have several advantages. First, they are easier to use than any known systems. Their use involves fewer steps, since there is no need to measure the water sample. Second, the reagent cap design permits complete mixing and is versatile. By flattening the "reagent bubble" all of the reagent is forced into the vial to mix with the water sample. The "reagent bubble" could hold the reagent in glass ampoules, plastic ampoules, plastic sacks, or a pill. Third, SMV disposables are relatively inexpensive to manufacture.

Several electroanalytical schemes can be used in conjunction with the disposable sensor 10 of the present invention.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. In combination with a monitoring device for determining the concentration of at least one metal in a water sample, a disposable sensor comprising a housing including a first section, a second section, and a flexible intermediate section therebetween, an ampoule disposed in the intermediate section and containing a reagent, means for forming a liquid seal between the first and second sections, means for disposing the water sample in the first section, and at least one electrode assembly disposed in the second section, wherein the intermediate section of the housing of the disposable sensor may be flexed to break the ampoule, wherein the seal may be broken between the first and second sections, such that the water sample mixes with the reagent and flows into the second section containing the electrode assembly, and wherein said at least one electrode assembly may be disposed in engagement with the monitoring device to determine the concentration of said at least one metal in the water sample.

2. The disposable sensor of claim 1, wherein the means for disposing the water sample in the first section of the housing further includes a top cap removably secured to the first section, and a top cavity for measuring the water sample, wherein the top cavity contains the water sample of a predetermined volume.

3. The disposable sensor of claim 2, wherein funnel shape walls surround the top cavity, wherein an upper edge of the funnel shaped walls comprises at least one notch, such that, once the water sample is poured into the top cavity, and the top cap is closed, any excess water runs out said notch.

4. The disposable sensor of claim 1, wherein the intermediate section of the housing further includes side walls having a series of annular ribs spaced apart longitudinally.

5. The disposable sensor of claim 4, wherein said annular ribs provide additional flexibility to the intermediate section of the housing to facilitate breaking of the ampoule while flexing the housing.

6. The disposable sensor of claim 1, wherein the housing is made of plastic.

7. The disposable sensor of claim 1, wherein the second section of the housing includes a lower chamber for disposing a mixture of the water sample and the reagent, wherein said at least one electrode assembly includes a first portion secured within said lower chamber, such that once the first portion of said at least one electrode assembly is immersed into the mixture of the water sample and the reagent, said at least one electrode assembly emits an electrical signal corresponding to the concentration of the metal in the water sample.

8. The disposable sensor of claim 7, wherein said at least one electrode assembly further includes a second portion protruded externally from a lower edge of the second section of the housing to engage the monitoring device, wherein a protective cap is removably secured to said lower edge of the second section of the housing, such that when the protective cap is removed and the second portion of said at least one electrode assembly engages the monitoring device, said monitoring device reads the emitted electrical signal corresponding to the concentration of said at least one metal in the water sample.

9. The disposable sensor of claim 8, wherein said at least one electrode assembly includes at least two, electrodes, wherein the monitoring device applies a predetermined electrical potential, series of potentials, or potential ramp between said at least two electrodes, and wherein said at least one electrode assembly emits an electrical signal corresponding to the concentration of the metal in the water sample in response to the predetermined electrical potential, series of potentials, or potential ramp.

10. The disposable sensor of claim 9, wherein the electrical signal may be emitted while the electrical potential is applied.

11. The disposable sensor of claim 9, wherein the electrical signal may be emitted after the electrical potential was applied.

12. The disposable sensor of claim 1, wherein at least two electrodes of said at least one electrode assembly are printed on a non-conductive substrate.

13. The disposable sensor of claim 1, wherein the monitoring device further includes a displaying means, and wherein the concentration of the metal in the water sample determined by the monitoring device is displayed by the displaying means.

14. The disposable sensor of claim 1, wherein the housing further includes a molded plastic part extending within the housing substantially through the intermediate section and the second section of the housing, and leaving a narrow space between the molded plastic part and a side wall of the housing to secure the ampoule in proper orientation, and wherein a slot is formed in a lower end of the molded plastic part, the electrode assembly being secured within said slot.

15. The disposable sensor of claim 1, wherein the ampoule may include a thin bag, which can be ruptured by flexing the disposable sensor.

16. In combination with a monitoring device for determining the concentration of a metal in a water sample, a disposable sensor comprising:

a plastic housing including a first section, a second section, and an intermediate section therebetween;

an ampoule disposed in the intermediate section and containing a reagent, the ampoule being held within the intermediate section in a predetermined orientation;

means for forming a liquid seal between the first and second sections;

means for disposing the water sample in the first section; and at least one electrode assembly disposed in the second section and comprising a non-conductive substrate and two electrodes printed thereon;

wherein the intermediate section of the housing of the disposable sensor may be flexed to break the ampoule and wherein the seal may be broken between the first and second sections, such that the water sample mixes with the reagent and flows into the second section containing said at least one electrode assembly;

wherein the first section of the housing includes a top cap removably secured to the first section, and having a top cavity for measuring the water sample, such that the top cavity contains the water sample of a predetermined volume;

wherein the intermediate section of the housing includes side walls having series of annular ribs spaced apart longitudinally, the annular ribs providing additional flexibility to the intermediate section of the housing to facilitate breaking of the ampoule while bending the housing along its longitudinal axis;

wherein the second section of the housing includes a lower chamber for disposing a mixture of the water sample and the reagent;

said at least one electrode assembly including a first portion and a second portion, the first portion being secured within said lower chamber, such that once the first portion of said at least one electrode assembly is immersed into the mixture of the water sample and the reagent, said at least one electrode assembly emits an electrical signal corresponding to the concentration of the metal in the water sample, and the second portion of said at least one electrode assembly extending externally from a lower edge of the second section of the housing to engage the monitoring device, wherein a protective cap is removably secured to said lower edge of the second section of the housing, such that when the protective cap is removed and the second portion of said at least one electrode assembly engages the monitoring device, said monitoring device reads the emitted electrical signal corresponding to the concentration of the metal in the water sample;

the monitoring device applying a predetermined electrical potential to the second portion of said at least one electrode assembly between said two electrodes, such that said at least one electrode assembly emits the electrical signal corresponding to the concentration of the metal in the water sample in response to the predetermined electrical potential, wherein said electrical potential may include a single electrical potential, a series of electrical potential, or a potential ramp; and a displaying means, wherein the concentration of the metal in the water sample determined by the monitoring device is displayed by the displaying means.

17. The disposable sensor of claim 16, wherein the said ampoule includes a frangible ampoule.

18. In combination with a monitoring device, a method for determining the concentration of a metal in a water sample, the method comprising the steps of:

providing a disposable sensor comprising a housing including a first section, a second section, and an intermediate section therebetween, providing an ampoule disposed in the intermediate section of the housing and containing a reagent, disposing at least one electrode as assembly in the second section of the housing, said at least one electrode assembly comprising a non-conductive substrate and at least two electrodes printed thereon, disposing the water sample in the first section of the housing, breaking the ampoule and the seal between the first and second sections of the housing, such that the water sample mixes with the reagent and flows into the second section of the housing containing said at least one electrode assembly, providing an electrical connection between said at least one electrode assembly and the monitoring device, applying a predetermined electrical potential to said at least one electrode assembly between said at least two electrodes to yield an electrical signal emitted by said at least one electrode assembly and corresponding to the concentration of the metal in the water sample in response to the predetermined electrical potential, reading the emitted electrical signal by the monitoring device, providing a displaying means, and displaying the concentration of the metal in the water sample by said displaying means.

19. The method of claim 18, further including the steps of providing the first section of the housing with a top cap removably secured to the first section, providing a top cavity for measuring the water sample, such that the top cavity contains the water sample of a predetermined volume.

20. The method of claim 19, further including the steps of providing the intermediate section of the housing with series of annular ribs spaced apart longitudinally and providing additional flexibility to the intermediate section of the housing to facilitate breaking of the ampoule while bending the housing along its longitudinal axis.

21. The method of claim 18, further including the steps of providing the second section of the housing with a lower chamber for disposing the mixture of the water sample and the reagent, providing said at least one electrode assembly with a first portion and a second portion, said first portion being secured within said lower chamber, such that once the first portion of said at least one electrode assembly is immersed into the mixture of the water sample and the reagent, said at least one electrode assembly emits an electrical signal corresponding to the concentration of the metal in the water sample, and said second portion being protruded externally from a lower edge of the second section of the housing to engage the monitoring device.

22. In combination with a monitoring device for determining the concentration of at least one metal in a water sample, a disposable sensor comprising at least one electrode assembly having a pair of electrodes, a cylindrical housing secured to said at least one electrode assembly by a lower end, and a cap removably secured to a top end of the cylindrical housing, the top end of the cylindrical housing having a plurality of circumferentially-spaced metering holes, the cap having a cylindrical sleeve and a top surface, a plurality of holes being disposed across the top surface of the cap, an ampoule, containing a reagent, being disposed above the top surface of the cap and being secured to the cap by a flexible cover, means for disposing the water sample in the housing, wherein when the cap is secured to the housing, the cylindrical sleeve of the cap seals the metering holes in the housing, and wherein the flexible cover may be flexed to break the ampoule, such that the reagent, contained in the ampoule, is forced into the housing through said holes in the top surface of the cap, and such that the water sample mixes with the reagent in the housing, and wherein said at least one electrode assembly may be disposed in engagement with the monitoring device to determine the concentration of said at least one metal in the water sample.

* * * * *